United States Patent [19]

Lumma, Jr.

[11] 4,091,098

[45] May 23, 1978

[54] 3-(1-PIPERAZINYL)-1,2,4-BENZOTRIAZINES AND N-OXIDES

[75] Inventor: William C. Lumma, Jr., Pennsburg, Pa.

[73] Assignee: Merck & Co., Inc., Rahway, N.J.

[21] Appl. No.: 790,363

[22] Filed: Apr. 25, 1977

[51] Int. Cl.$^2$ .................... C07D 251/72; A61K 31/53
[52] U.S. Cl. ........................................ 424/249; 544/183
[58] Field of Search ..................... 544/183; 424/249

[56] References Cited

U.S. PATENT DOCUMENTS

| 3,265,693 | 8/1966 | Lowrie | 260/247.5 |
|---|---|---|---|
| 3,272,818 | 9/1966 | Lowrie | 260/268 |
| 3,470,182 | 9/1969 | Hardtmann et al. | 260/256.4 |

FOREIGN PATENT DOCUMENTS

| 840,904 | 8/1976 | Belgium | 260/250 |
|---|---|---|---|
| 1,440,722 | 6/1976 | United Kingdom | 260/268 |

OTHER PUBLICATIONS

Rodriguez et al., European J. of Pharmacology, 24 (1973) pp. 164–171.

*Primary Examiner*—John M. Ford
*Attorney, Agent, or Firm*—Rudolph J. Anderson, Jr.; Mario A. Monaco; Martin L. Katz

[57] ABSTRACT

3-(1-Piperazinyl)-1,2,4-benzotriazines, N-oxides and pharmaceutically acceptable salts thereof have serotoninmimetic activity. They are prepared by treating 3-halo-1,2,4-benzotriazines or N-oxides thereof with piperazine.

6 Claims, No Drawings

3-(1-PIPERAZINYL)-1,2,4-BENZOTRIAZINES AND N-OXIDES

BACKGROUND OF THE INVENTION

This invention is concerned with 3-(1-piperazinyl)-1,2,4-benzotriazines, N-oxides and pharmaceutically acceptable salts thereof which demonstrate serotoninmimetic activity and hence are useful as anorectic, antidepressant, analgesic and hypnotic agents.

Several piperazinyl heterocycles are known in the art, for example, 2-(1-piperazinyl)quinoxalines (British Pat. No. 1,440,722); 4-(1-piperazinyl)quinazolines (U.S. Pat. No. 3,470,182); 2-(1-piperazinyl)quinolines (Rodriquez et al., European Journal of Pharmacology 24, 164–171 (1973); 4-(1-piperazinyl)cinnolines (U.S. Pat. Nos. 3,265,693 and 3,272,818); and 2-(1-piperazinyl)pyrazines (Belgian Pat. No. 840,904). With this invention there is provided a group of 3-(1-piperazinyl)-1,2,4-benzotriazines with serotoninmimetic properties and which exhibit anorectic antidepressant, analgesic and hypnotic activity. There are also provided processes for preparing the novel compounds, pharmaceutical compositions comprising the novel compounds, and methods of treatment comprising the administration of such compounds and compositions.

DETAILED DESCRIPTION OF THE INVENTION

The novel compounds of this invention have structural formula:

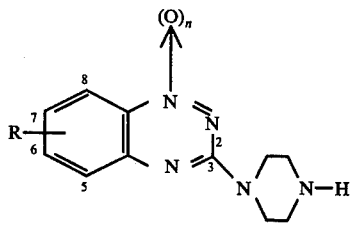

or a pharmaceutically acceptable salt thereof, wherein $n$ is 0 is 1;

R is hydrogen, halo, such as chloro, bromo, or fluoro, trifluoromethyl, lower alkyl, especially $C_{1-3}$ alkyl, lower alkylthio, especially $C_{1-3}$ alkylthio, lower alkoxy, especially $C_{1-3}$ alkoxy, or cyano.

In a preferred embodiment of the novel compounds, R is on the 6- or 7-position.

Also included within the scope of the present invention are non-toxic pharmaceutically acceptable salts. Such acid addition salts of the novel compounds are formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, sulfuric acid, phosphoric acid, nitric acid, isethionic acid or the like.

The novel process of this invention comprises reacting a 1,2,4-benzotriazine or N-oxide substituted in the 3-position with a suitable leaving group such as a halogen, trialkylammonium, alkylsulfonyl, phenylsulfonyl, alkylsulfinyl or phenylsulfinyl, and piperazine. The 3-substituted-1,2,4-benzotriazine or N-oxide, preferably a 3-chloro compound and piperazine are mixed in a solvent, and allowed to react until the reaction is essentially complete. The solvent used as the reaction medium is preferably a polar solvent such as water, aqueous solvent mixtures, oxygenated solvents such as lower alkanols comprising methanol, ethanol, n-propanol, isopropanol, butyl alcohols, nitrogen containing solvents such as N,N-diloweralkylamides as, for example, dimethylacetamide, dimethylformamide and mixtures of such materials with water.

The reaction is conducted at a temperature of from 0°–100° C. or at the reflux temperature of the reaction medium for a period of from 15 minutes to 24 hours. A period of from 1–5 hours at a temperature of from 15°–50° C. is preferred.

The N-oxide compounds of this invention are reduced by a variety of reducing agents, especially by treatment with zinc in acidic medium such as aqueous ammonium chloride at room temperature to about 50° C. for 5–24 hours.

A further embodiment of this invention is a method of producing an anorectic effect in patients in need of such treatment that comprises administering a therapeutically effective amount of the compounds and compositions of the present invention. Typically the dosage level ranges from about 0.1 to about 500 mg./day, and preferably is from 0.1 to about 100 mg./day of the active principle of the present invention.

The compounds of this invention also find utility as antidepressants, analgesics and hypnotic agents and for such purposes are administered as described above. Pharmaceutical compositions comprising a novel compound as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from about 0.1 to about 100 mg.

EXAMPLE 1

3-(1-Piperazinyl)-1,2,4-benzotriazine-1-oxide hydrochloride

To a slurry of 2-chloro-1,2,4-benzotriazine-1-oxide (12.0 g., 0.066 mol.) in 100 ml. of isopropanol is added 11.4 g. (0.132 mol.) of anhydrous piperazine with cooling under $N_2$. The exothermic reaction is moderated at 35°–40° C. for 15 min., and then stirred 2 hours at 20°–25° C. The orange precipitate is collected by suction and partitioned between chloroform and aqueous sodium carbonate. After drying, the $CHCl_3$ extract is concentrated under vacuum to an oil which is taken up in a boiling mixture of 200 ml. of hexane and 200 ml. benzene. The solution is filtered and concentrated under vacuum, and the residue is dissolved in 150 ml. ethanol and treated with 10 ml. of 10N anhydrous ethanolic-HCl. The yellow crystalline crude hydrochloride (9.2 g.) is recrystallized from methanol and then from aqueous ethanol to give pure 3-(1-piperazinyl)-1,2,4-benzotriazine-1-oxide hydrochloride, m.p. 306°–307° C. (dec.).

Employing the procedure substantially as described in Example 1, but substituting for the 2-chloro-1,2,4-benzotriazine-1-oxide used therein equimolecular amounts of the 2-chloro-1,2,4-benzotriazines described in Table I, there are produced the 3-(1-piperazinyl)-

1,2,4-benzotriazines also described in Table I, in accordance with the following reaction.

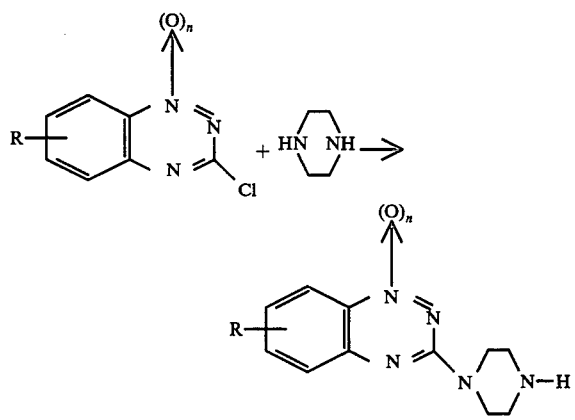

TABLE I

| Compound | R | n |
|---|---|---|
| 1 | 7-Cl | 1 |
| 2 | 7-CF₃ | 1 |
| 3 | 7-CH₃ | 1 |
| 4 | 7-SCH₃ | 1 |
| 5 | 6-CF₃ | 1 |
| 6 | H | 0 |
| 7 | 7-Cl | 0 |
| 8 | 7-CF₃ | 0 |
| 9 | 7-CH₃ | 0 |
| 10 | 7-SCH₃ | 0 |
| 11 | 6-CF₃ | 0 |
| 12 | 7-OCH₃ | 0 |
| 13 | 7-CN | 0 |

EXAMPLE 2

3-(1-Piperazinyl)-1,2,4-benzotriazine hydrochloride

To a cooled suspension of 2.68 g. (0.010 mol.) of 3-(1-piperazinyl)-1,2,4-benzotriazine-1-oxide hydrochloride in a stirred solution of 0.75 g. (0.014 mol.) of ammonium chloride in 25 ml. of water is added 1.0 g. of powdered zinc. After 5 hours, 25 ml. of additional water and 1.0 g. more of ammonium chloride is added and stirring is continued a total of 24 hours. The pH of the mixture is adjusted to 10 with sodium carbonate and the product is extracted with chloroform. The chloroform extract is washed with saturated sodium chloride solution, dried over sodium carbonate, filtered and concentrated under vacuum to a red oil which is dissolved in absolute ethanol (50 ml.) and treated with 2 ml. of cold 10N anhydrous ethanolic-HCl. The crude yellow hydrochloride which separates is recrystallized from methanol-water to give 2.0 g. of 3-(1-piperazinyl)-1,2,4-benzotriazine hydrochloride, m.p. 324°–325° C. (dec.)

Employing the procedure substantially as described in Example 2, but substituting for the 3-(1-piperazinyl)-1,2,4-benzotriazine-1-oxide hydrochloride used therein, an equimolecular amount of the 3-(1-piperazinyl)-1,2,4-benzotriazine-1-oxide hydrochlorides described in Table I, (compounds 1-5) there are produced, respectively, the 3-(1-piperazinyl)-1,2,4-benzotriazine hydrochlorides also described in Table I, (compounds 7-11) in accordance with the following reaction:

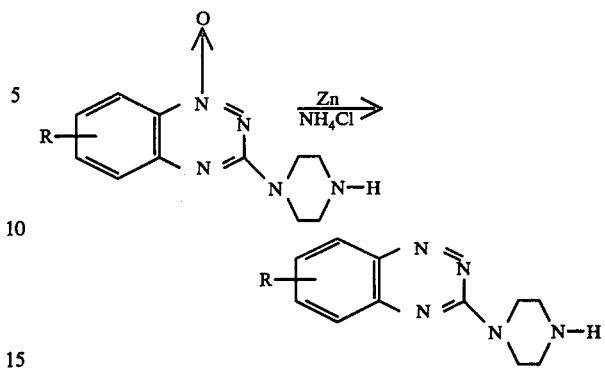

EXAMPLE 3

Preparation of Capsule Formulation

| Ingredient | Milligrams per Tablet |
|---|---|
| 3-(1-piperazinyl)-1,2,4-benzotriazine-1-oxide hydrochloride | 6 |
| Starch | 87 |
| Magnesium stearate | 7 |

The active ingredient, starch and magnesium stearate are blended together. The mixture is used to fill hard shell capsules of a suitable size at a fill weight of 100 milligrams per capsule.

EXAMPLE 4

Preparation of Tablet Formulation

| Ingredient | Milligrams per Tablet |
|---|---|
| 3-(1-piperazinyl)1,2,4-benzotriazine hydrochloride | 12 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° C. The dry granules are passed through a No. 16 screen. The mixture is lubricated with magnesium stearate and compressed into tablets in a suitable tableting machine. Each tablet contains 12 milligrams of active ingredient.

What is claimed is:

1. A compound of structural formula:

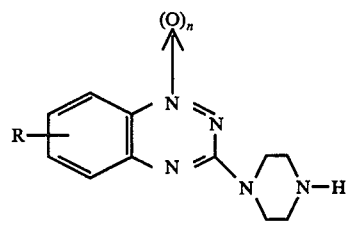

or a pharmaceutically acceptable salt thereof, wherein n is 0 or 1; R is hydrogen, halo, trifluoromethyl, lower alkyl, lower alkylthio, lower alkoxy or cyano.

2. The compound of claim 1, wherein R is the 6- or 7-position, or a pharmaceutically acceptable salt thereof.

3. The compound of claim 1 which is 3-(1-piperazinyl)-1,2,4-benzotriazine-1-oxide or a pharmaceutically acceptable salt thereof.

4. The compound of claim 1 which is 3-(1-piperazinyl)-1,2,4-benzotriazine or a pharmaceutically acceptable salt thereof.

5. A method of decreasing food intake in a patient in need of such treatment comprising the administration of an effective amount of a compound of structural formula:

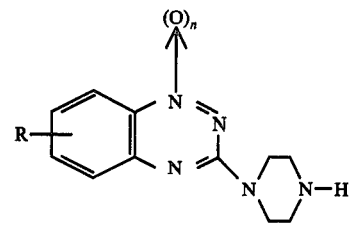

or a pharmaceutically acceptable salt thereof, wherein
$n$ is 0 or 1;
R is hydrogen, halo, trifluoromethyl, lower alkyl, lower alkylthio, lower alkoxy or cyano.

6. A pharmaceutical composition comprising a pharmaceutical carrier and an effective amount of a compound of structural formula:

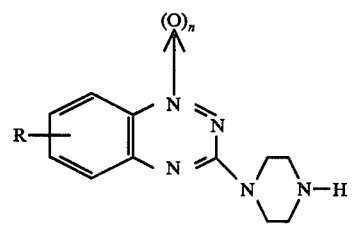

or a pharmaceutically acceptable salt thereof, wherein
$n$ is 0 or 1;
R is hydrogen, halo, trifluoromethyl, lower alkyl, or lower alkylthio, lower alkoxy or cyano.

* * * * *